United States Patent [19]
Mannion et al.

[11] Patent Number: 5,807,556
[45] Date of Patent: *Sep. 15, 1998

[54] METHODS OF PREVENTING DEGENERATION OF MYOPLASTIES

[75] Inventors: John D. Mannion, Mt. Laurel, N.J.; Michael G. Magno, Oxford, Pa.

[73] Assignee: Thomas Jefferson University, Philadelphia, Pa.

[*] Notice: This patent issued on a continued prosecution application filed under 37 CFR 1.53(d), and is subject to the twenty year patent term provisions of 35 U.S.C. 154(a)(2).

[21] Appl. No.: 683,228

[22] Filed: Jul. 18, 1996

[51] Int. Cl.$^6$ .......................... A61K 38/18; C07K 14/50; A61N 1/18

[52] U.S. Cl. ................. 424/198.1; 514/56; 530/399; 536/21; 607/3; 607/50

[58] Field of Search ................ 514/12, 56; 424/548, 424/198.1; 530/399; 536/21; 607/3, 50

[56] References Cited

PUBLICATIONS

Baffour et al., "Enhanced angiogenesis and growth of collaterals by in vivo administration of recombinant basic fibroblast growth factor in a rabbit model of acute lower limb ischemia: Dose–response effect of basic fibroblast growth factor," *J. Vasc. Surg.* 1992, 16:181–191.
Bailey et al., "Chronic Stimulation Enhances Extramyocardial Collateral Bloof Flow After a Cardiomyoplasty", *Ann. Thorac. Surg.* 1993 56:1045–1053.
Banai et al., "Angiogenic–Induced Enhancement of Collateral Bloof Flow to Ischemic Myocardium by Vascular Endothelial Growth Factor in Dogs", *Circulation* 1994, 89:2183–2189.
Battler et al., "Intracoronary Injection of Basic Fibroblast Growth Factor Enhances Angiogenesis in Infarcted Swince Myocardium", *JACC* 1993, 22:2001–2006.
Blood et al. "Basic Fibroblast Growth Factor Identified in Chronically Stimulated Cardiomyoplasties", *Ann. Thorac. Surg.* 1994, 58:1320–1326.
Casscells et al., "Isolation, Characterization and Localization of Heparin–binding Growth Factors in the Heart", *J. Clin. Invest.* 1990, 85:433–441.
Durham et al., "Regional Perfusion of Latissimus Dorsi Pedicle Flaps in Dynamic Cardiomyopolasty", *JACC* 1992, 19:353A.
Eldelman et al., "Perivascular and intravenour administration of basic fibroblast growth factor: Vascular and solid organ deposition", *Proc. Nat'l Acad. Sci.* 1993, 90:1513–1517.
Folkman J. and Klagsbrun M., "Angiogenic Factors" *Science* 1987, 235:442–447.
Galloway et al., "Do ischemic hearts stimulate endothelial cell growth?", *Surgery* 1984, 96:435–439.
Gospodarowicz et al., "Structural Characterization and Biological Functions of Fibroblast Growth Factor", *Endocrine Review* 1987, 8:95–114.
Kalil–Filho et al., "Magnetic Resonance Imaging Evaluation of Chronic Changes in Latissimus Dorsi Cardiomyoplasty", *Circulation* 1994, 90:II–102—II–106.
Kratz et al., "The relation between latissimus dorsi skeletal muscle strucure and contractile function after cardiomyoplasty", *J. Thorac. Cardiovasc. Surg.* 1994, 107:868–878.
Levin et al., "Alterations in Regional Mechanics and Blood Flow Can Explain Lack of Benefit During Cardiomyoplasty", *Circulation* 1991, 94:II–355.
Lucas et al., "Long–Term Follow–Up (12 to 35 Weeks) After Dynamic Cardiomyoplasty", *JACC* 1993, 22:758–767.
Magovern et al., "Operation for Congestive Heart Failure: Transplantation, Coronary Artery Bypass, and Carciomyoplasty", *Ann. Thorac. Surg.* 1993, 56:418–25.
Magovern et al., "Paced Skeletal Muscle for Dynamic Cardiomyoplasty", *Ann. Thorac. Surg.* 1988, 45:614–619.
Mannion et al., "Techiques to Enhance Extramyocardial Collateral Blood Flow After a Cardiomyoplasty", *Annals of Surgery* 1993 218:544–554.
Mannion et al., "Acute Electrical Stimulation Increases Extramyocardial Collateral Blood Flow After a Cardiomyoplasty", *Ann. Thorac. Surg.* 1993 56:1351–1358.
Moreira et al., "Current Expectations in Dynamic Cardiomyoplasty", *Ann. Thorac. Surg.* 1993, 55:299–303.
Morrow et al., "Increased Expression of Fibroblast Growth Factors in a Rabbit Skeletal Muscle Model of Exercise Conditioning", *J. Clinical investigation* 1990, 85:1816–1820.
Pu et al. "Enhanced Revascularization of the Ischemic Limb by Angiogenic Therapy", *Circulation* 1993, 88:208–215.
Radermecker et al., "Influence of Tension Reduction and Peripheral Dissection on Histologic, Biochemical and Bioenergetic Profiles, and Kinetics of Skeletal Muscle Fast––to–Slow Transformation", *J. Card. Surg.* 1991, 6:Supp. 195–203.
Spirito et al., "Immunohistochemical Localization of Basic and Acidic Fibroblast Growth Factors in the Developing Rat Heart", *Circulation* 1991, 84:322–332.
Takeshita et al., "Therapeutic Angiogenesis", *J. Clin. Invest.* 1994, 93:662–670.
Unger et al., "Basic fibroblast growth factor enhances myocardial collateral flow in a canine model", *Am J. Physiol.* 1994, 266:H1588–H1595.
Yanagiasawa–Miwa et al., "Salvage of Infarcted Myocardium by Angiogenic Action of Basic Fibroblast Growth Factor", *Science* 1992, 257:1401–1403.
DeFeudis, F.V. 1991, Life Science, 49: 689–705.
Harada, K. et al. 1994, J. Clin. Invest. 94:623–630.
Mannion, et al., "Effects of Collateral Blood Vessel Ligation and Electrical Conditioning on Blood Flow in Dog Latissimus Dorsi Muscle", *J. Surg. Res*, 47:322–340, 1989.

*Primary Examiner*—Toni R. Scheiner
*Assistant Examiner*—Nancy A. Johnson
*Attorney, Agent, or Firm*—Law Offices of Jane Massey Licata

[57] ABSTRACT

Methods of reducing the degeneration of a tissue resulting from mobilization with or without chronic, continuous electrical stimulation by administering basic fibroblast growth factor or heparin to the tissue are provided.

3 Claims, No Drawings

METHODS OF PREVENTING DEGENERATION OF MYOPLASTIES

INTRODUCTION

This invention was made in the course of research sponsored by the National Institutes of Health. The U.S. Government may have certain rights in this invention.

This application is a continuation of provisional application 60/001,213, filed Jul. 18, 1995.

BACKGROUND OF THE INVENTION

Myoplasty is a procedure in which skeletal muscle is surgically moved from its normal position in the body and applied to another location for the purposes of reconstruction of damaged tissues and improving the function of visceral organs such as the heart, anal sphincter, urinary bladder sphincter and urinary bladder. A degree of degeneration occurs as the result of the surgical mobilization. When this procedure is performed to improve the function of a visceral organ, continuous or frequently repeated electrical stimulation of the skeletal muscle is usually required. This type of electrical stimulation has also been associated with additional degeneration of the muscle and loss of function.

Surgical procedures for myoplasty involve severing the connections of the muscle to the surrounding structures including many of the blood vessels, nerves and tendons. Severing tendons causes a loss of resting tension and results in atrophy (Radermecker et al. *J. Card.* Surg. 1991, 6: Supp. 195–203). For the improvement of visceral organ function, at least one neuro-vascular pedicle is preserved. However, the blood supply to the muscle is still compromised. Electrically stimulating this muscle to contract forces the muscle to work without adequate blood supply resulting in further injury to the muscle.

Chronic ischemic injury of the latissimus has been recognized as contributing to a lack of efficacy in both clinical and experimental cardiomyoplasties (Magovern et al. *Ann. Thorac. Surg.* 1988, 45:614–619; Moreira et al. *Ann. Thorac. Surg.* 1993, 55:299–303; Kalil-Filho et al. *Circulation* 1994, 90: II–102–II–106; Magovern et al. *Ann. Thorac. Surg.* 1993, 56:418–25; Kratz et al. *J. Thorac. Cardiovasc. Surg.* 1994, 107:868–878; Lucas et al. *JACC* 1993, 22:758–767; Levin et al. *Circulation* 1991, 84: II–355; Tobin et al. *Proc. Cardiovasc. Sci. and Tech. Conf.*, Assoc. for Adv. Med. Inst. 1991, 69; Mannion et al. *J. Surg. Res.* 1989, 47:322–340; Durham et al. *JACC* 1992, 19:353A). Further, chronic stimulation decreases the blood flow of the latissimus dorsi muscle itself.

Some work has been done to overcome the problem. A delay period between mobilization and the onset of electrical stimulation was shown to minimize ischemic damage, but the complete prevention of damage was not demonstrated (Mannion et al. *J. Surg. Res.* 1989, 47:322–340). Currently, a period of two or more weeks is allowed following the surgical procedure before the myoplasty is stimulated to provide time for new blood vessels to grow into the myoplasty. The muscle is then conditioned by gradually increasing the stimulus frequency and intensity. However, this regimen has not proven to be adequate as degeneration and failure may begin even 6 months after the procedure.

It has now been found that administration of basic fibroblast growth factor (bFGF) or heparin as adjuncts to myoplasty significantly reduce the degeneration resulting from mobilization and chronic electrical stimulation of the muscle used for the myoplasty.

SUMMARY OF THE INVENTION

An object of the present invention is to provide a method of reducing the degeneration of a tissue resulting from mobilization with or without chronic, continuous electrical stimulation of the tissue by administering to the tissue an effective amount of either basic fibroblast growth factor (bFGF) or heparin. In a preferred embodiment, the bFGF or heparin is administered following myoplasty to protect a skeletal muscle, such as the latissimus dorsi, from degeneration resulting from mobilization followed by chronic, continuous electrical stimulation.

DETAILED DESCRIPTION OF THE INVENTION

Administration of bFGF or heparin into the arterial supply of a chronically stimulated myoplasty significantly reduces the degeneration resulting from mobilization and electrical stimulation of the muscle used for the myoplasty. In the present invention, a method of reducing the degeneration of a tissue resulting from mobilization with or without chronic, continuous electrical stimulation of the tissue is provided which comprises administering to the tissue an effective amount of bFGF or heparin. By "effective amount" it is meant a concentration of bFGF or heparin which is found to decrease the amount of degeneration observed in a tissue following mobilization with or without chronic, continuous electrical stimulation. Such concentrations can be routinely determined in accordance with the teachings provided herein. In a preferred embodiment, the bFGF or heparin is administered intraarterially either as a bolus injection or infusion, respectively, to decrease the degeneration of skeletal muscle which results from mobilization with or without chronic, continuous electrical stimulation of the skeletal muscle.

Examples wherein this adjunct therapy is particularly useful include, but are not limited to, myoplasties such as cardiomyoplasty, skeletal muscle ventricle and aortomyoplasty, surgical procedures for fecal incontinence, urinary incontinence and urinary voiding in paralyzed patients, functional electrical stimulation of limbs in paralyzed patients, reconstructive surgery in which prevention of muscle degeneration would improve the outcome, and other degenerative muscle diseases. Cardiomyoplasty is a procedure wherein skeletal muscle, such as the latissimus dorsi, is stimulated every second or third heart beat to mechanically assist a failing heart. Skeletal Muscle Ventricle is a procedure wherein a skeletal muscle is mobilized on its neurovascular pedicle and wrapped spirally around a cone shaped stent. After a period of time, the stent is removed and the skeletal muscle ventricle is connected to the circulation and stimulated to contract. With the addition of valves the skeletal muscle functions as a heart. In aortomyoplasty, skeletal muscle is wrapped around the thoracic aorta. By stimulating the muscle to contract during diastole, the muscle functions similarly to balloon counterpulsation. For fecal incontinence, skeletal muscle is wrapped around the rectum and stimulated continuously. The stimulator is turned off to permit defecation. Similarly, for urinary bladder incontinence, skeletal muscle is wrapped around the urethra and stimulated constantly. The stimulator is again turned off to permit voiding. In patients who have lost control and tone of the detrusor muscle as a result of a spinal cord injury, the muscle can be electrically stimulated to contract periodically to aid in urination. bFGF and heparin are also believed to be useful as adjuncts in functional electrical stimulation of motor nerves in patients who have been paralyzed as a result of spinal cord injury. It is also believed that bFGF or heparin administration following reconstructive surgery will prevent degeneration of tissue mobilized during the surgery.

Basic fibroblast growth factor (bFGF) is a member of a family of peptide growth factors that have been demonstrated to modulate angiogenesis during growth and development (Spirito et al. *Circulation* 1991, 84:322–332; Folkman J. and Klagsbrun M. *Science* 1987, 235:442–447). However, its only normal, physiological role in adults appears to be during pregnancy, follicle development and ovulation (Gospodarowicz et al. *Endocrine Review* 1987, 8:95–114). Endogenous bFGF expression appears to be increased in electrically stimulated skeletal muscle (Morrow et al. *J. Clinical investigation* 1990, 85:1816–1820) and in ischemic myocardium (Galloway et al. *Surgery* 1984, 96:435–439; Casscells et al. *J. Clin. Invest.* 1990, 85:433–441). bFGF has also been identified in chronically stimulated cardiomyoplasties (Blood et al. *Ann. Thorac. Surg.* 1994, 58:1320–1326). Infusion of angiogenic agents such as bFGF has been reported to increase revascularization of ischemic skeletal muscle (Baffour et al. *J. Vasc. Surg.* 1992, 16:181–191; Pu et al. *Circulation* 1993, 88:208–215; Takeshita et al. *J. Clin. Invest.* 1994, 93:662–670) and myocardium (Yanagisawa-Miwa et al. *Science* 1992, 257:1401–1403; Battler et al. *JACC* 1993, 22:2001–2006; Unger et al. *Am. J. Physiol.* 1994, 266:H1588–H1595; Banai et al. *Circulation* 1994, 89:2183–2189).

bFGF has also been reported to stimulate muscle cell proliferation while inhibiting terminal differentiation into actual muscle fibers.

Heparin and heparin-like molecules function as regulators of cell growth and neovascularization. Heparin protects endogenous heparin binding growth factors which have myogenic properties from degradation. Heparin also stimulates the release of these growth factors from extracellular matrix storage sites. Previous studies with heparin administration following myoplasty, however, showed no improvement in blood flow in the latissimus dorsi (Mannion et al. *Annals of Surgery* 1993 218:544–554).

It has now been found, however, that administration of either bFGF or heparin improves the morphological appearance of chronically stimulated latissimus in animals following myoplasty.

Latissimus dorsi cardiomyoplasties were performed in goats as described in Example 1. Chronic myocardial ischemia as then induced and the area at risk for ischemia defined as described in Example 2. In these experiments, a group of animals, referred to herein as the 2 Hz-bFGF group, received a bolus injection of human recombinant bFGF administered into the subclavian artery on post operative days 14, 21, 28 and 35 as described in Example 3. bFGF has a short half-life in vivo (Eldelman et al. *Proc. Nat'l Acad. Sci.* 1993, 90:1513–1517). By giving bolus injections weekly, inhibition of terminal differentiation was minimized. These animals were also subjected to chronic, continuous electrical stimulation (2 Hz) for 5 to 8 weeks post-surgery beginning on post-operative day 5–8 as described in Example 5.

Photomicrographs from sections from the transposed left latissimus dorsi muscle samples from these animals were prepared and examined as described in Example 7 and compared to photomicrographs prepared from: a group of animals undergoing the surgery without any subsequent electrical stimulation, referred to herein as the 0 Hz group; a group of animals undergoing the surgery and subjected to chronic, continuous electrical stimulation for 5 to 8 weeks post-surgery beginning on post-operative day 5–8 as described in Example 5, referred to herein as the 2 Hz group; and, a group of animals administered intra-arterial heparin as described in Example 4 and also subjected to chronic, continuous electrical stimulation for 5 to 8 weeks post-surgery beginning on post-operative day 5–8 as described in Example 5, referred to herein as the 2 Hz-HEP group. Fatty infiltration as a percentage of total muscle, which is indicative of fiber death, is shown in Table 1 for each group.

TABLE 1

|  | 0 Hz | 2 Hz | 2 Hz-HEP | 2 Hz-bFGF |
| --- | --- | --- | --- | --- |
| MEAN | 16.43 | 56.95 | 20.36 | 11.60 |
| Std. Error | 6.22 | 9.16 | 5.03 | 3.04 |
| # of animals | 7 | 5 | 7 | 6 |

The inter-fiber connective tissue was minimal in samples from animals in the 0 Hz group. The blood vessels and nerves seen were all well preserved. No evidence of subintimal hyperplasia of arterioles was observed. Further there was only moderate mononuclear cell infiltrate in 2 of the samples and virtually none in the other 5.

Samples from animals in the 2 Hz-HEP group exhibited a mixed degree of mononuclear cellular infiltration. Three animals showed minimal cellular infiltrations. It was moderate in one, and moderately heavy in three. Blood vessels and nerves in all seven animals appeared well preserved. No subintimal hyperplasia of arterioles was seen. Overall, the quantity of interfiber connective tissue appeared similar to that of the 0 Hz animals.

Samples from animals in the 2 Hz-bFGF also exhibited a mixed degree of mononuclear infiltration. Minimal mononuclear infiltration was observed in three animals. One animal had a moderate amount, and it was moderately heavy in the remaining 2 animals. Blood vessels and nerves were seen in all latissimus dorsi sections reviewed and appeared well preserved. No subintimal hyperplasia was observed in the small or medium sized blood vessels. Further, there was appreciably less extensive fatty changes and fibrosis in these animals as compared to animals in the 2 Hz group.

All samples from the left latissimus of animals in the 2 Hz group had a moderate mononuclear cellular infiltrate. Further, approximately 3 times as much muscle was replaced by fat in this group as compared with animals in the 0 Hz, 2 Hz-4bFGF or 2 Hz-HEP group. As shown in Table 2, the amount of interfiber connective tissue present was also greater than in the 2 Hz-bFGF group. Blood vessels and nerves were observed in all animals and appeared well preserved. Significant subintimal hyperplasia was not seen in arterioles.

TABLE 2

| Connective Tissue % of Total Muscle | 2 Hz | 2 Hz-bFGF |
| --- | --- | --- |
| MEAN | 20.65 | 8.24 |
| Std. Error | 3.28 | 2.14 |
| # of animals | 5 | 7 |

Comparison of the 0 Hz and 2 Hz group indicates that chronic stimulation significantly increased the amount of damage compared to surgery alone. As can be seen, however, both heparin and bFGF treatment were associated with minimal amounts of fiber loss, similar to that observed in the 0 Hz group. With regard to fibrosis, there was significantly less connective tissue in the 2 Hz-bFGF group than in the 2 Hz group (see Table 2). Thus, treatment with bFGF or heparin ameliorates the degeneration associated with mobilization and chronic, continuous electrical stimulation of tissues. The amount of heparin demonstrated to improve morphological appearance in electrically stimulated tissues is lower than amounts which result in anticoagulation.

In 4 animals of the 2 Hz-bFGF group, further quantitative evaluation of the latissimus was carried out by measuring capillary density, extracellular collagen, fiber size, and the capillary/fiber ratio as described in Example 7, Quantitative Assessment of the Latissimus. Muscle biopsies were taken from the mid-latissimus of all 4. In two animals, biopsies were also taken from the proximal and distal latissimus.

The general histological appearance of the latissimus was assessed from Hematoxylin and Eosin (H & E) stained sections. The right latissimus dorsi was not mobilized or stimulated. It served as a control for the chronically stimulated left latissimus. The right latissimus dorsi was found to be of excellent quality, with no cellular infiltrate. There was no fiber drop out. Each specimen demonstrated a minimal amount of perimysial connective tissue.

The left latissimus muscles of 5 of the 8 animals were similar in quality to the right latissimus and were rated as "excellent." Muscle quality was rated as "good" in the 3 other animals. Fiber drop out was less than 1% in one animal and less than 25% in the remaining 7 animals. Cellular infiltrate was minimal in 7 of 8 animals and moderate in the remaining animal. There was no evidence of subintimal hyperplasia.

Quantitative assessment of connective tissue was performed on the chronically stimulated left latissimus muscle treated with bFGF and unstimulated, right latissimus. Based on the silver impregnation stain, there was no change in connective tissue of the left latissimus when compared to unstimulated control right latissimus. Also, there were no statistically significant differences in fiber size, capillary density, or capillary/fiber ratio. Thus, bFGF administration preserved the muscle's architecture.

Regional differences in the capillary/fiber ratio were examined in 2 animals of the 2 Hz-bFGF group. For the right (unstimulated) latissimus, the ratio was the same for the proximal, mid and distal regions. However, the ratio for the proximal left (stimulated) latissimus was 3 times greater than that for the right latissimus and greater than that for the mid and distal regions of the left latissimus. The increase in the ratio was due primarily to higher capillary densities.

bFGF administration was also demonstrated to significantly improve the perfusion of the chronically stimulated latissimus muscle after cardiomyoplasty. Hemodynamic parameters and latissimus dorsi blood flow determined for 2 Hz-bFGF animals are compared with values previously reported for: the 0 Hz group (Mannion et al. *Ann. Thorac. Surg.* 1993 56:1351–1358); the 2 Hz group (Bailey et al. *Ann. Thorac. Surg.* 1993 56:1045–1053); and, the 2 Hz-HEP group (Mannion et al. *Annals of Surgery* 1993 218:544–554), in Table 3.

TABLE 3

| Parameter | 0 Hz | 2 Hz | 2 Hz-HEP | 2 Hz-bFGF |
| --- | --- | --- | --- | --- |
| Mean Arterial Pressure (mm Hg) | 118.7 | 80.8 | 108.0 | 120.6 |
| Std. Error | 5.8 | 6.7 | 6.0 | 5.0 |

TABLE 3-continued

| Parameter | 0 Hz | 2 Hz | 2 Hz-HEP | 2 Hz-bFGF |
| --- | --- | --- | --- | --- |
| # of animals | 9 | 10 | 5 | 8 |
| Heart Rate (beat/min) | 115.7 | 82.5 | 100.0 | 88.3 |
| Std. Error | 7.6 | 5.4 | 13 | 6.5 |
| # of animals | 9 | 10 | 5 | 8 |
| Cardiac Output (ml/min) | 3295 | 3060 | 3840 | not determined |
| Std. Error | 772 | 388 | 847 | not determined |
| # of animals | 3 | 10 | 5 | |
| Latissimus Dorsi Blood Flow (ml/g/min) | 0.030 | 0.042 | 0.040 | 0.114 |
| Std. Error | 0.010 | 0.007 | 0.020 | 0.029 |
| # of animals | 9 | 10 | 5 | 7 |

No significant differences between the blood flows for the 0 Hz, 2 Hz and 2 Hz-HEP groups were observed. However, flows for the 2 Hz-bFGF group were significantly greater than the flows for the unstimulated and 2 Hz animals. Because of the relatively large variability and smaller sample size, the 2 Hz-HEP animals were not found to significantly differ from animals in the 2 Hz-bFGF group.

Further, bFGF treatment maintained a level of vascularity that was sufficient to support a three fold increase in blood flow during chronic stimulation compared with that seen in response to chronic stimulation in cardiomyoplasties without bFGF treatment.

Applications in Coronary Artery Disease

Regional myocardial blood flows for the normal, chronically ischemic and infarcted myocardium in the 2 Hz-bFGF group are presented in Table 4.

TABLE 4

REGIONAL MYOCARDIAL BLOOD FLOW

| Parameter | Acute Occlusion | Chronic Occlusion |
| --- | --- | --- |
| Normal Myocardial Blood Flow (ml/g/min) | | |
| mean | 0.6676 | 1.0446 |
| Std. Error | 0.1623 | 0.1648 |
| n | 6 | 8 |
| Chronic Ischemic Myocardial Blood Flow (ml/g/min) | | |
| mean | 0.1281 | 0.7660 |
| Std. Error | 0.0620 | 0.1704 |
| n | 6 | 8 |
| Infarct Blood Flow (ml/g/min) | | |
| mean | 0.1228 | 0.1876 |
| Std. Error | 0.0632 | 0.2235 |
| n | 3 | 5 |

Blood flows measured in the chronic ischemic zone during acute occlusion of the coronary artery were low indicating few native collaterals. After chronic occlusion, ischemic zone blood flow tended to lower (75%), but not significantly so, than that of the normal myocardium. This level of flow indicates that collaterals (both intramyocardial and latissimus derived) had formed. Only 5 goats had infarcts based on regional myocardial flow (flow less than 30% of normal zone flow 7 weeks post-operatively).

The portion of ischemic zone blood flow derived from the latissimus was determined as described in Example 6. Flow from the latissimus dorsi averaged 42.8%±15.7 of normal myocardial blood flow. In one animal, the latissimus delivered blood flow to the chronically ischemic myocardium that was equal to 100% of the normal myocardial flow. The total flow delivered to the heart by the latissimus graft averaged 5.2±1.5 ml/min (n=5). Virtually all of this flow was delivered to the viable portion of the risk area.

The blood flow to ischemic myocardium was partitioned into the contributions from pre-existing collaterals, newly developed intra-coronary collaterals, and latissimus derived collaterals. The flow from pre-existing collaterals was significantly lower in the 2 Hz-bFGF than in the 2 Hz group. The flow from intra-coronary collaterals is about the same in both groups suggesting that bFGF administered to the latissimus did not increase the development of intra-coronary collaterals. The flow from the latissimus derived collaterals in the 2 Hz-bFGF group is almost twice that of the 2 Hz group. These data suggest that bFGF administration into the latissimus dorsi can stimulate the formation of extracardiac collaterals.

The following nonlimiting examples are provided to further illustrate the present invention.

EXAMPLES

Example 1: Latissimus Dorsi Cardiomyoplasty

Under sterile conditions, a latissimus dorsi cardiomyoplasty was prepared in accordance with procedures described by Mannion et al. *Annals of Surgery* 1993, 218:544–554. An intramuscular electrode was woven around the ramifications of the thoracodorsal nerve (Medtronics, Minneapolis, Minn.) and connected to a pulse generator (Itrel, model no. 7421, Medtronics, Minneapolis, Minn.).

Example 2: Chronic Myocardial Ischemia

Chronic myocardial ischemia was induced by placing an ameroid constrictor around a branch of the circumflex coronary artery. Over the course of two to three weeks, the amaroid constrictor absorbs water, and slowly occludes the coronary artery.

The area at risk for ischemia was defined by injecting microspheres into the left atrium during a temporary occlusion of the branch of the circumflex artery. This injection also served to measure pre-existing intra-coronary collateral flow to the risk area.

Example 3: bFGF Administration

A size 4 French silastic catheter was inserted into the subclavian artery, upstream to the origin of the thoracodorsal artery, through a left supraclavicular incision. The catheter was secured with a purse-string suture, and connected to a vascular access port hub implanted subcutaneously in the neck. Bolus injections of 80 $\mu$g of human recombinant bFGF (Synergen, Boulder, Colo.) were administered into the subclavian artery four times between post-operative days 10 and 35. To maintain patency, the catheter was flushed with 10 ml of heparinized saline (4 units heparin/ml).

Example 4: Heparin Administration

An osmotic pump (Alzet Corp., Palo Alto, Calif.) was implanted subcutaneously into the neck. A catheter connected to the pump was inserted into the left subclavian artery as described in Example 3. Heparin was then infused at a rate of 25 to 50 U/hour directly into the subclavian artery of the animal for a 28 day period as described by Mannion et al. *Annals of Surgery* 1993 218:544–554.

Example 5: Latissimus Dorsi Stimulation

Chronic, continuous electrical stimulation was begun between the 5th and 8th postoperative day. The pulse generator was initially set at 0.5 Hz and 3 volts. The frequency was gradually increased to 2 Hz over 10 days. The voltage was adjusted to maintain a palpable contraction.

Example 6: Hemodynamic and Blood Flow Measurements

After the 6 week period of electrical stimulation, the animals were anesthetized with sodium pentobarbital and ventilated artificially with 100% oxygen. Arterial blood pressure and the electrocardiogram were monitored and the time tension index (TTI is equal to systolic pressure×heart rate) was calculated as an index of myocardial oxygen consumption. Regional blood flows were measured by injecting 15 million microspheres of one color into the left atrium.

Latissimus derived collateral blood flow to the heart was measured by simultaneously injecting 7.5 million microspheres of another color into the subclavian artery. The microspheres were 15 microns in diameter and were too large to recirculate. Therefore, they could only enter the myocardium through collaterals with the latissimus. Latissimus derived collateral flow was calculated according to the formula described by Mannion et al. *Annals of Surgery* 1993, 218:544–554.

Example 7: Histological Analysis and Morphometry

The general histological appearance of the latissimus was assessed from Hematoxylin and Eosin (H & E) stained sections. Vascularity of the latissimus was determined from capillary/fiber density ratios calculated from morphometric data. Mason's trichrome stain was used to identify areas of myocardial infarction.

General Latissimus Morphology

The right and left latissimus muscles were evaluated subjectively from H & E stained sections. Biopsies were taken from the proximal, mid, and distal (attached to heart) latissimus dorsi and placed in formalin. The samples were embedded in "Paraplast" and 7 micrometer sections were cut. Each slide was reviewed at 100× and 200× magnification. The following qualitative observations were made: 1) general morphology, rated as excellent, good or poor, 2) presence or absence of cellular infiltrate, and 3) fiber dropout or fatty changes. The percentage of muscle fibers replaced by fat was estimated and categorized as none, 1–25%, 26–50%, and greater than 50%. Fatty areas were unstained and had a size similar to the muscle fiber they replaced.

Quantitative Assessment of the Latissimus

In 4 animals, a quantitative evaluation of the latissimus was carried out by measuring capillary density, extracellular collagen, fiber size, and the capillary/fiber ratio. Muscle biopsies were taken from the mid-latissimus of all 4. In two animals, biopsies were taken from the proximal and distal latissimus, also.

The biopsies were placed in Carnoys solution overnight, dehydrated through graded ethanols, cleared in xylenes, and embedded in paraplast. Ten serial sections 5 $\mu$m in thickness were cut from each block, mounted on glass slides, deparaffinized, and rehydrated.

Sections were stained with: 1) GSA-B4 lectin (capillary density); 2) silver stain (extracellular collagen); and 3) H &

E (fiber size and density). Capillary/fiber ratio were calculated from the capillary and fiber densities. For each measurement, 10 random fields for each muscle slide were analyzed with computer assisted techniques.

GSA-B4 (Sigma Chemical, St. Louis, Mo.) conjugated to horse-radish peroxidase was diluted 1:50 in PBS, and incubated on the tissue sections for 2 hours in a humidified chamber at 37° C. The slides were thoroughly rinsed in PBS. Sites of bound lectin were visualized by incubation in a 3', 3'-diaminobenzidine-hydrogen peroxide substrate medium followed by 2 additional rinses in PBS. For a negative control, sections were incubated with non-conjugated lectin.

The stained sections were mounted on an inverted microscope (IM-35, Ziess, Munich, West Germany) and imaged at a final magnification of 400×. The image was input through a high resolution video camera (Dage 68, Michigan City, Ind.) connected to a computer image analysis system (IBAS 2000, Ziess/Kontron, Munich, West Germany). For each section, 10 random fields with an area 25,390 $\mu m^2$ per field were analyzed.

Using computer aided stereology, the number of capillaries per unit area (numerical density) was computed. A computer generated test frame automatically discriminated the capillary profiles and determined the number of profiles within the test area using exclusion-edge principles. Capillary diameter was calculated by measuring the area of a stained vessel, transforming this area into a circle, and computing the diameter.

H & E stained sections were viewed under epifluorescent illumination to determine fiber size. The silver stained sections were used to determine extracellular connective tissue. Computer assisted morphometry was used for both.

Myocardial Infarction

After euthanasia, the heart was removed. The ventricles and attached latissimus were cut into 4 concentric rings. Full thickness sections were embedded in paraffin and stained with Mason's trichrome. Sections were mounted on a Reichert Diastar microscope and imaged at 25× magnification. The image was input through an RGB/YC/NTSC video camera (Worldwide Video, Inc, Boyertown, Pa.) connected to Bioquant System IV True Color Image Analysis system (R & M Biometrics, Nashville, Tenn.). Color thresholds were set manually to identify the portion of the section that was stained blue (for collagen) and red (for viable tissue). The system measured each area independently and calculated the percent infarct of each section.

Example 8: Statistical Analysis

Comparisons were made using paired or unpaired t-tests as appropriate. A Bonferroni correction was made for multiple comparisons.

Example 9: Efficacy of Skeletal Muscle Pedicle Grafts to Revascularize Myocardium in Patients with Inoperable Coronary Artery Disease Revascularization of ischemic myocardium of patients with severe distal coronary artery disease by chronically stimulated latissimus pedicle graft with bFGF administration as an adjunct treatment will be assessed. Three groups of patients including: 1) chronically stimulated cardiomyoplasty with bFGF; 2) chronically stimulated cardiomyoplasty without bFGF treatment; and 3) unoperated patients with similar severity of disease will be studied.

As a measure of efficacy of this procedure to alleviate stress induced ischemia, myocardial lactate production will be examined. Patients with inoperable triple vessel disease are expected to have a lactate extraction of 20% at rest and −10% during cardiac pacing at 140 beats/minute on preoperative evaluation. Patients which have undergone cardiomyoplasty without bFGF treatment are expected to have a myocardial lactate extraction of approximately 0–5% during pacing 6 months postoperatively. This degree of improvement is clinically relevant. bFGF treated patients are expected to have a significantly greater myocardial lactate extraction of approximately 10–15%.

Safety of the procedure will also be assessed based upon a comparison of the mortality and morbidity of the groups undergoing cardiomyoplasty with and without bFGF treatment as compared to the unoperated control group at the end of the initial period (1 year). Morbidity will be determined by the number of hospitalizations for i) all causes, ii) cardiac therapy, and iii) number of ICU days for cardiac therapy. Mortality will be tracked as time of patient death i) due to any cause, and ii) due to cardiac death.

Changes in patient's functional status and quality of life compared to their pre-operative data and the progression of the unoperated controls will also be documented.

What is claimed is:

1. A method of reducing the degeneration of a skeletal muscle resulting from mobilization of the tissue comprising administering to the tissue undergoing mobilization an effective amount of basic fibroblast growth factor combined with subjecting said tissue to chronic electrical stimulation.

2. The method of claim 1 wherein the basic fibroblast growth factor is administered as a bolus injection.

3. A method of reducing the degeneration of a skeletal muscle resulting from mobilization of the tissue comprising administering to the tissue undergoing mobilization an effective amount of heparin combined with subjecting said tissue to chronic electrical stimulation.

* * * * *